United States Patent [19]

Teutsch et al.

[11] 4,233,297
[45] * Nov. 11, 1980

[54] NOVEL Δ⁴-ANDROSTENES

[75] Inventors: Jean G. Teutsch, Pantin; Roger Deraedt, Les Pavillons-sous-Bois, both of France

[73] Assignee: Roussel Uclaf, Paris, France

[*] Notice: The portion of the term of this patent subsequent to Sep. 18, 1996, has been disclaimed.

[21] Appl. No.: 52,489

[22] Filed: Jun. 27, 1979

[30] Foreign Application Priority Data

Jul. 13, 1978 [FR] France .................. 78 20971

[51] Int. Cl.³ .............................. A61K 31/56
[52] U.S. Cl. .................. 424/243; 260/397.45; 260/239.55 C
[58] Field of Search .................. 260/397.45; 424/243

[56] References Cited

U.S. PATENT DOCUMENTS 4,168,306  9/1979  Teutsch et al. .................. 260/397.45

OTHER PUBLICATIONS

JACS (1961) vol. 83, pp. 4663–4664, Article by Fried et al.

Primary Examiner—Elbert L. Roberts

Attorney, Agent, or Firm—Hammond & Littell, Weissenberger and Muserlian

[57] ABSTRACT

Novel Δ⁴-androstenes of the formula

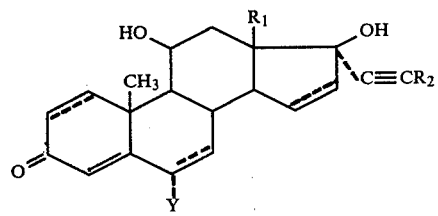

wherein $R_1$ is alkyl of 1 to 3 carbon atoms, Y is selected from the group consisting of hydrogen, fluorine and methyl, $R_2$ is selected from the group consisting of saturated and unsaturated alkyl of 1 to 12 carbon atoms, —$CF_3$, aryl of 6 to 12 carbon atoms and aralkyl of 7 to 12 carbon atoms and the dotted lines in the A and B rings indicate the optional presence of one or two double bonds in the 1(2) and 6(7)-positions with the proviso that when $R_1$ is methyl, $R_2$ is saturated or unsaturated alkyl and the B ring is saturated, Y is methyl having anti-inflammatory activity and novel intermediates.

30 Claims, No Drawings

NOVEL Δ⁴-ANDROSTENES

STATE OF THE ART

Related steroids are described in French patent No. 1,349,113, U.S. Pat. No. 3,010,957 and copending, commonly assigned U.S. patent application Ser. No. 878,907 filed Feb. 17, 1978, now U.S. Pat. No. 4,168,306.

OBJECTS OF THE INVENTION

It is an object of the invention to provide the novel Δ⁴-androstenes of formula I and a novel process for their preparation and novel intermediates.

It is another object of the invention to provide novel anti-inflammatory compositions and to a novel method of treating inflammation in warm-blooded animals.

These and other objects and advantages of the invention will become obvious from the following detailed description.

THE INVENTION

The novel compounds of the invention are Δ⁴-androstenes of the formula wherein $R_1$ is alkyl of 1 to 3 carbon atoms, Y is selected from the group consisting of hydrogen, fluorine and methyl, $R_2$ is selected from the group consisting of saturated and unsaturated alkyl of 1 to 12 carbon atoms, —$CF_3$, aryl of 6 to 12 carbon atoms and aralkyl of 7 to 12 carbon atoms and the dotted lines in the A and B rings indicate the optional presence of one or two double bonds in the 1(2) and 6(7)-positions with the proviso that when $R_1$ is methyl, $R_2$ is saturated or unsaturated alkyl and the B ring is saturated, Y is methyl.

$R_1$ is preferably methyl or ethyl but may be isopropyl or n-propyl. Examples of $R_2$ are saturated alkyl such as methyl, ethyl, n-propyl, isopropyl, n-butyl, isobutyl, tert.-butyl, n-pentyl, n-hexyl, 2-methyl-pentyl, 2,3-dimethylbutyl, n-octyl and 2,2-dimethyl-hexyl; unsaturated alkyl such as vinyl, isopropenyl, isobutenyl, allyl and 2-methyl-allyl; aryl such as phenyl; and aralkyl such as benzyl.

Among the preferred compounds of formula I are those wherein $R_1$ is methyl, those wherein the A ring has a double bond in the 1(2)-position, those wherein the B ring has a double bond in the 6(7)-position and those wherein Y is hydrogen or methyl. A preferred specific compound is 21-methyl-Δ¹,⁴,⁶-pregnatriene-20-yne-11β,17β-diol-3-one.

The novel process of the invention for the preparation of the compounds of formula I comprises reacting in the presence of alkali metal tertiary alcoholate a compound of the formula

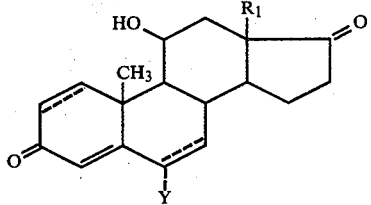

wherein $R_1$, Y and the dotted lines have the above definitions with a compound of the formula $HC≡CR_2$ to obtain the corresponding compound of formula I.

In a preferred mode of the process of the invention, the starting compound has the formula wherein $R_1$ is alkyl of 1 to 3 carbon atoms. The preferred alkali metal tertiary alcoholate is an alkali metal tert.-butylate or teramylate, such as sodium tert.-amylate, sodium tert.-butylate, potassium tert.-butylate, lithium tert.-butylate, potassium tert.-amylate and lithium tert.-amylate.

A variation of the process of the invention to form a compound of formula I comprises reacting a compound of the formula

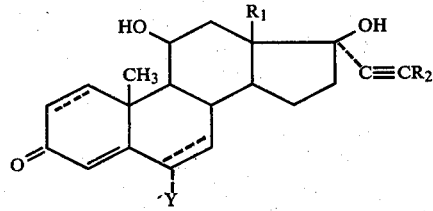

wherein $R_1$ and Y have the above definitions K is a blocked ketone in the form of a ketal or oxime and L is alkyl of 1 to 12 carbon atoms with a compound of the formula $$T-C≡CR_2 \qquad V$$

wherein T is selected from the group consisting of lithium, potassium and HalMg— to form a compound of the formula

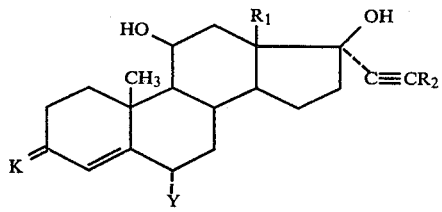

a compound of the formula

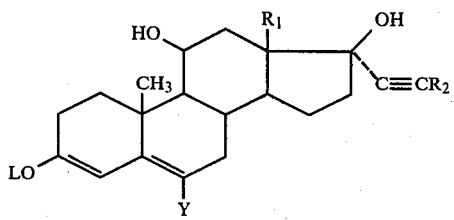

and reacting either the compound of formulae VI or VII with an acid hydrolysis agent to obtain a compound of the formula

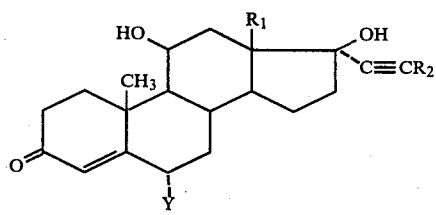

or with an agent able to free the ketone group and create a $\Delta^{4,6}$-double bond system to obtain a compound of the formula

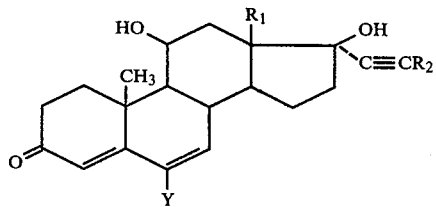

or with an agent able to free the ketone group and create a $\Delta^{1,4,6}$-double bond system to obtain a compound of the formula

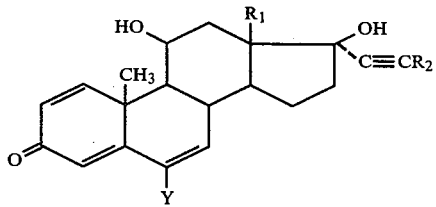

In the variation of the process described above, K is preferably a cyclic alkyl ketal of 2 to 4 carbon atoms such as ethylene ketal or propylene ketal or a dialkyl ketal of 1 to 4 alkyl carbon atoms such as dimethylketal or diethylketal. K may also be a blocked ketone in the form of an oxime, preferably —NOH or —NOAlK wherein AlK is alkyl of 1 to 4 carbon atoms. L is preferably methyl, ethyl or n-propyl and Hal is preferably bromine.

The acid hydrolysis agent is preferably hydrochloric acid, sulfuric acid, acetic acid, citric acid or p-toluene sulfonic acid. The agent capable of freeing the ketone group and forming the $\Delta^{4,6}$-double bond system is preferably a p-benzoquinone derivative such as 2,3-dichloro-5,6-dicyanobenzoquinone and chloranil and the reaction is effected in aqueous acetone. Also useful is a biochemical means such as Arthrobacter Simplex. The agent capable of freeing the ketone group and forming a $\Delta^{1,4,6}$-double bond system is again a p-benzoquinone derivative such as chloranil or 2,3-dichloro-5,6-dicyano-benzoquinone and the reaction is effected in benzene.

The starting compounds of formulae II, III and IV are generally known compounds and may be prepared by known processes such as those described in French Pat. No. 1,359,611 or No. 1,222,424 or U.S. Pat. No. 3,010,957 or No. 3,072,684. 3-ethoxy-6-methyl-$\Delta^{3,5}$-androstadiene-11$\beta$-ol-17-one is a novel intermediate.

The novel anti-inflammatory compositions of the invention are comprised of an anti-inflammatorily effective amount of at least one compound of formula I and an inert pharmaceutical carrier or excipient. The compositions may be in the form of tablets, dragees, cachets, capsules, granules, emulsions, syrups, suppositories, injectable solutions or suspensions, pomades, creams, gels and aerosol preparations.

Examples of suitable excipients are talc, starch, aqueous and non-aqueous vehicles, fatty bodies of animal or vegetable origin, paraffinic derivatives, glycols, diverse wetting agents, emulsifiers and dispersants and preservatives.

Because of their anti-inflammatory activity, the compositions are useful for the treatment of polyarthritis, arthrose, lombalgia, and local inflammatory reactions such as edemas, dermatosis, pruritsis, diverse forms of eczema and solar erythema. The preferred activity is a topical anti-inflammatory activity.

The novel method of treating inflammation in warm-blooded animals, including humans, comprises administering to warm-blooded animals an anti-inflammatorily effective amount of at least one compound of formula I. The compounds may be administered orally, rectally, parenterally and preferably topically to the skin or mucous. The useful posology varies especially depending upon the person to be treated and the complaint concerned. It can be, for example, between 1 and 4 applications inclusive per day of an ointment containing from 0.1% to 5% of product of example 2. The compound of Example 2 is orally administered at a dose of 0.2 to 20 mg/kg.

In the following examples there are described several preferred embodiments to illustrate the invention. However, it should be understood that the invention is not intended to be limited to the specific embodiments.

EXAMPLE 1

21-methyl-$\Delta^{4,6}$-pregnadiene-20-yne-11$\beta$,17$\beta$-diol-3-one

STEP A:

3-ethoxy-21-methyl-$\Delta^{3,5}$-pregnadiene-11$\beta$,17$\beta$-diol

Propyne was bubbled at 0° C. through 70 ml of a solution of 0.75 M of ethyl magnesium bromide in tetrahydrofuran for 2 hours and the temperature was allowed to rise to room temperature after which a mixture of 3.45 g of 3-ethoxy-$\Delta^{3,5}$-androstadiene-11$\beta$-ol-17-one (Belgium Pat. No. 864,170) and 14 ml of dry tetrahydrofuran was added thereto. The mixture was held at 20°-25° C. for 45 minutes and was then poured into a cold ammonium chloride solution. The mixture was extracted with ether and the ether phase was washed with aqueous saturated sodium chloride solution, dried over sodium sulfate and evaporated to dryness under reduced pressure to obtain 3-ethoxy-21-methyl-$\Delta^{3,5}$-pregnadiene-11$\beta$,17$\beta$-diol which was used as is for the next step.

STEP B:
21-methyl-$\Delta^{4,6}$-pregnadiene-20-yne-11$\beta$,17$\beta$-diol-3-one 5 ml of distilled water were added to a solution of 4 g of the product of Step A in 100 ml of acetone and then 4.8 g of 2,3-dichloro-5,6-dicyanobenzoquinone were added thereto. The mixture was stirred at room temperature for one hour and was then poured into a saturated sodium bicarbonate solution. The mixture was extracted with methylene chloride and the organic phase was washed with aqueous 0.5 M sodium thiosulfate solution, dried over sodium sulfate and evaporated to dryness to obtain 3.8 g of residue. The latter was chromatographed over silica gel and was eluted with a 1-1 benzene-ethyl acetate mixture to obtain a product with an Rf=0.25. The latter was crystallized from isopropyl ether to obtain 21-methyl-$\Delta^{4,6}$-pregnadiene-20-yne-11$\beta$,17$\beta$-diol-3-one melting at 200° C.

Analysis: $C_{22}H_{28}O_3$; molecular weight=340.466; Calculated: %C 77.6, %H 8.29; Found: 77.8, 8.3

EXAMPLE 2

21-methyl-$\Delta^{1,4,6}$-pregnatriene-20-yne-11$\beta$,17$\beta$-diol-3-one

A solution of 3.7 g of 3-ethoxy-21-methyl-$\Delta^{3,5}$-pregnadiene-20-yne-11$\beta$,17$\beta$-diol and 50 ml of benzene was poured under nitrogen with stirring into a solution containing 6.8 g of 2,3-dichloro-5,6-dicyano-benzoquinone and the mixture was stirred for 25 minutes, was washed with an aqueous saturated sodium bicarbonate solution, with aqueous 0.5 M sodium thiosulfate solution. The organic phase was dried and evaporated to dryness under reduced pressure to obtain 2.75 g of raw product. The latter was chromatographed over silica gel and was eluted with a 1-1 benzene-ethyl acetate mixture to obtain 1.2 g of product with an Rf=0.20. The latter was crystallized from an isopropyl ether-acetone-methylene chloride mixture to obtain 819 mg of 21-methyl-$\Delta^{1,4,6}$-pregnatriene-20-yne-11$\beta$,17$\beta$-diol-3-one melting at 216° C.

Analysis: $C_{22}H_{26}O_3$; molecular weight=338.45; Calculated: %C 78.07, %H 7.74; Found: 77.9, 77

EXAMPLE 3

21-phenyl-$\Delta^{1,4}$-pregnadiene-20-yne-11$\beta$,17$\beta$-diol-3-one

A mixture of 2.91 g of potassium tert.-butylate, 2.75 ml of phenylacetylene and 100 ml of dioxane was stirred at room temperature for one hour and then a mixture of 3 g of $\Delta^{1,4}$-androstadiene-11$\beta$-ol-3,17-dione (prepared by process of U.S. Pat. No. 3,010,957) and 30 ml of dioxane were added thereto. The suspension was stirred for 2 hours and aqueous acetic acid and water were added thereto. The mixture was extracted with methylene chloride and the organic phase was washed with aqueous saturated sodium bicarbonate solution, dried over sodium sulfate and evaporated to dryness to obtain 4.25 g of raw product. The latter was chromatographed over silica gel and was eluted with a 6-4 benzene-ethyl acetate mixture to obtain 1.265 g of product with a Rf=0.20. The latter was crystallized from a methylene chloride-isopropyl ether mixture to obtain 21-phenyl-$\Delta^{1,4}$-pregnadiene-20-yne-11$\beta$,17$\beta$-diol-3-one melting at 262° C. and having a specific rotation of $[\alpha]_D^{20}=-21°\pm2°$ (c=0.7% in CHCl$_3$).

EXAMPLE 4

21-trifluoromethyl-$\Delta^{1,4}$-pregnadiene-20-yne-11$\beta$,17$\beta$-diol-3-one A solution of 2.1 g of $\Delta^{1,4}$-androstadiene-11$\beta$-ol-3,17-dione, 35 ml of anhydrous tetrahydrofuran and 3.5 ml of hexamethylphosphotriamide was stirred at −70° C. under nitrogen while bubbling a current of trifluoromethyl-acetylene therethrough and then a solution of 3.4 g of 96% potassium tert.-butylate, 70 ml of tetrahydrofuran and 3.5 ml of hexamethylphosphotriamide was added thereto dropwise. The mixture was poured into an aqueous ammonium chloride solution and the mixture was extracted with ether. The ether phase was dried and evaporated to dryness under reduced pressure. The residue was chromatographed over silica gel and was eluted with a 6-4 benzene-ethyl acetate mixture to obtain 2.7 g of product. The latter was crystallized from an isopropyl ether-methylene chloride mixture to obtain 2.248 g of 21-trifluoromethyl-$\Delta^{1,4}$-pregnadiene-20-yne-11$\beta$,17$\beta$-diol-3-one melting at 254°-225° C. and having a specific rotation of $[\alpha]_D^{20}=-6.5°\pm1.5°$ (c=0.75% in CHCl$_3$).

EXAMPLE 5

6$\alpha$,21-dimethyl-$\Delta^{1,4}$-pregnadiene-20-yne-11$\beta$,17$\beta$-diol-3-one Propyne was bubbled for 90 minutes through a solution of 200 ml of tetrahydrofuran and 10.3 g of 96% potassium tert.-butylate and the mixture was then stirred for a few hours after which 20 ml of hexamethylphosphotriamide were added thereto. A solution of 5.75 g of 6$\alpha$-methyl-$\Delta^{1,4}$-androstadiene-11$\beta$-ol-3,17-dione (prepared by process of French Pat. No. 1,359,611) in 60 ml of tetrahydrofuran was added thereto at −15° C. and the mixture was stirred for 4 hours at −15° C. The mixture was poured into aqueous hydrochloric acid and the mixture was extracted with ether. The ether phase was washed with water, dried and evaporated to dryness to obtain 6.05 g of residue. The latter was chromatographed over silica gel and was eluted with an 8-2 methylene chloride-acetone mixture. The product was chromatographed a second time over silica gel and was eluted with a 6-4 benzene-ethyl acetate mixture. The product was crystallized from isopropyl ether to obtain 1.105 g of 6$\alpha$,21-dimethyl-$\Delta^{1,4}$-pregnadiene-20-yne-11$\beta$,17$\beta$-diol-3-one melting at 196° C. and having a specific rotation of $[\alpha]_D^{20}=-14°\pm2°$ (c=0.5% in CHCl$_3$).

EXAMPLE 6

6,21-dimethyl-$\Delta^{4,6}$-pregnadiene-20-yne-11$\beta$,17$\beta$-diol-3-one

STEP A:
3-ethoxy-6-methyl-$\Delta^{3,5}$-androstadiene-11$\beta$-ol-17-one 0.25 ml of a solution of 480 mg of p-toluene sulfonic acid in 50 ml of ethanol were added with stirring under nitrogen at 50° C. to a suspension of 1.80 g of 6$\alpha$-methyl-Δ⁴-androstene-11β-ol-3,17-dione in 10 ml of ethanol and 2 ml of triethoxymethane and after 5 minutes, 0.4 ml of triethylamine were added thereto. The mixture was cooled on an ice bath and water was added thereto dropwise. The mixture was vacuum filtered and the recovered product was washed with a 7-3 ethanol-water mixture and dried to obtain 1.66 g of 3-ethoxy-6-methyl-$\Delta^{3,5}$-androstadiene-11β-ol-17-one with an Rf=0.55 (1-1 benzene-ethyl acetate mixture).

STEP B:
6,21-dimethyl-$\Delta^{4,6}$-pregnadiene-11β,17β-diol-3-one

A current of propyne was bubbled under nitrogen with stirring into a solution of 1.15 M of ethyl magnesium bromide in tetrahydrofuran at 0° C. and the temperature was allowed to return to room temperature. The mixture was stirred for 90 minutes at room temperature and 6.3 g of the product of Step A were added thereto. The mixture was stirred for another 90 minutes and was poured into an aqueous ammonium chloride-ice mixture. The mixture was extracted with ether and the ether phase was washed with aqueous sodium bicarbonate solution, dried and evaporated to dryness under reduced pressure to obtain 4.7 g of residue. The latter was dissolved in 100 ml of acetone and 5 ml of water and 2.5 g of 2,3-dichloro-5,6-dicyanobenzoquinone were added thereto. The mixture was poured into aqueous sodium bicarbonate solution and the resulting mixture was extracted with methylene chloride. The organic phase was washed with sodium thiosulfate solution, dried over sodium sulfate and evaporated to dryness under reduced pressure. The residue was chromatographed over silica gel and was eluted with a 1-1 benzene-ethyl acetate mixture to obtain 2.95 g of 6,21-dimethyl-$\Delta^{4,6}$-pregnadiene-11β,17β-diol-3-one.

Analysis: $C_{23}H_{30}O_3$; molecular weight=354.47; Calculated: %C 76.76, %H 8.57; Found: 76.6, 8.7

RMN Spectrum (deuterochloroform-60 MHz): $CH_3$- 81.5 Hz, 71.5 Hz and 110 Hz; H at 270 Hz; and ethylenic hydrogen at 352 Hz.

EXAMPLE 7

21-phenyl-$\Delta^4$-pregnene-20-yne-11β,17β-diol-3-one 7.2 ml of phenylacetylene were added dropwise to a solution of 40 ml of 1.3 M n-butyllithium hexane and 40 ml of anhydrous tetrahydrofuran and then 3 g of 3-ethoxy-$\Delta^{3,5}$-androstadiene-11β-ol-17-one were added thereto. The mixture was stirred at room temperature for 17 hours and was then poured into aqueous ammonium chloride solution. The mixture was extracted with ether and the ether extracts were dried and evaporated to dryness. The residue was chromatographed over silica gel and was eluted with a 1-1 benzene-ethyl acetate mixture containing 0.2% of triethylamine to obtain a product with an Rf=0.35. The latter was treated for 30 minutes with a solution of 125 ml of methanol and 25 ml of N hydrochloric acid solution. The mixture was poured into water and the mixture was extracted with methylene chloride and the extracts was dried over sodium sulfate and evaporated to dryness under reduced pressure. The product was purified by chromatography to obtain 1.1 g of 21-phenyl-$\Delta^4$-pregnene-20-yne-11β,17β-diol-3-one with a specific rotation of $[\alpha]_D^{20}=-4°\pm2°$ (c=0.7% in $CHCl_3$).

EXAMPLE 8

6,21-dimethyl-$\Delta^{1,4,6}$-pregnatriene-20-yne-11β,17β-diol-3-one

Propyne was bubbled at 0° C. with stirring for 30 minutes under an inert gas through a solution of 1.15 M of ethyl magnesium bromide in tetrahydrofuran and the temperature was allowed to rise while the bubbling was continued for 90 minutes. Then, 4.5 g of 3-ethoxy-6-methyl-$\Delta^{3,5}$-androstadiene-11β-ol-17-one were added thereto and the mixture was stirred for one hour at 20° C. and was then poured in an aqueous ammonium chloride solution at 0° C. The mixture was extracted with ether and the organic phase was washed with aqueous sodium bicarbonate solution, dried and evaporated to dryness. The 4.3 g of residue was dissolved in 80 ml of benzene and a solution of 9 g of 2,3-dichloro-5,6-dicyano-benzoquinone in 200 ml of benzene was added thereto. The mixture was stirred at 20° C. for 30 minutes and was then poured into aqueous sodium bicarbonate solution. The mixture was extracted with ether and the ether phase was washed with 0.5 N sodium thiosulfate solution, with sodium bicarbonate solution, was dried and evaporated to dryness. The 3.4 g of residue was chromatographed over silica gel and eluted with a 3-7 benzene-ethyl acetate mixture to obtain 2.95 g of 6,21-dimethyl-$\Delta^{1,4,6}$-pregnatriene-20-yne-11β,17β-diol-3-one which after crystallation from methanol melted at 148° C.

Analysis: $C_{23}H_{28}O_3.CH_3OH$; Calculated: %C 74.97, %H 8.39; Found: 75.3, 8.4

I.R. Spectrum ($CHCl_3$): Presence of OH, —C≡C—$CH_3$ and C=O at 1660–1653 cm$^{-1}$; C=C at 1608 cm$^{-1}$.

U.V. Spectrum (ethanol): Max at 228 nm, ε=12,700 Inflex. at 250 nm, ε=8,600 Max. at 304 nm, ε=10,700

EXAMPLE 9

A pomade for topical application was prepared with 1.5 g of 21-methyl-$\Delta^{1,4,6}$-pregnatriene-20-yne-11β,17β-diol-3-one and sufficient excipient of lanolin and vaseline for a total weight of 100 g.

EXAMPLE 10

PHARMACOLOGICAL DATA

In the following tests, the compounds used were 21-methyl-$\Delta^{1,4,6}$-pregnatriene-20-yne-11β,17β-diol-3-one (product A) and 21-trifluoromethyl-$\Delta^{1,4}$-pregnadiene-20-yne-11β,17β-diol-3-one (Product B).

A. Oral Anti-inflammatory Activity

The anti-inflammatory test used was the classical granuloma test with the modified technique of Meier et al [Experienta, Vol. 6 (1950), p. 469] with the test compounds used in the form of an aqueous dispersion containing 0.25% of carboxymethylcellulose and 0.20% of Polysorbate 80. Female Wistar rats weighing between 100 and 110 g received an implantation of 2 cotton pellets weighing 10 mg each under the thorax skin and oral administration of the test compounds started after the implantation for 2 days with 2 administrations per day, 16 hours after the last ingestion or on the third day, the animals were killed and the pellets were removed with the formed granuloma tissue. They were weighed fresh and then after 18 hours at 60° C. and the weight of the granuloma was determined by substracting the initial weight of the cotton. The $AD_{50}$ which is the dose which inhibited by 50% the granuloma was 10 and 4 mg/kg for products A and B, respectively which means that the products exhibited a good anti-inflammatory activity when orally administered.

B. Local Dermic Activity

The dermic activity was determined with the croton edema test of Tonelli et al [Endocrinology, Vol. 77 (1965), p. 625] wherein edema was provoked in mice by application of croton oil to an ear. Mice in one group received an application of croton oil on the right ear and mice in a second group received an application of croton oil containing products A and B on the right ear and nothing was applied to the left ear of either group. After 6 hours, the ears were cut off and weighed and the difference in weight between the right ears and the left ears was the degree of inflammation. The $AC_{50}$ or the active concentration which lessened the edema provoked by the croton oil by 50% as compared to the controls group was 0.07 and 0.3 mg/kg for products A and B, respectively which indicates that the products have a remarkable local anti-inflammatory activity.

Various modifications of the products and method of the invention may be made without departing from the spirit or scope thereof and it is to be understood that the invention is intended to be limited only as defined in the appended claims.

We claim:

1. $\Delta^4$-androstenes of the formula

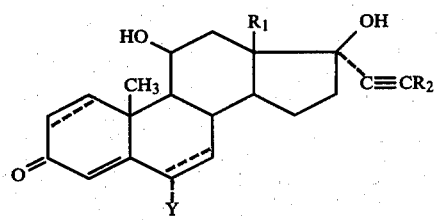

wherein $R_1$ is alkyl of 1 to 3 carbon atoms, Y is selected from the group consisting of hydrogen, fluorine and methyl, $R_2$ is selected from the group consisting of saturated and unsaturated alkyl of 1 to 12 carbon atoms, —$CF_3$, aryl of 6 to 12 carbon atoms and aralkyl of 7 to 12 carbon atoms and the dotted lines in the A and B rings indicate the optional presence of one or two double bonds in the 1(2) and 6(7) positions with the proviso that when $R_1$ is methyl, $R_2$ is saturated or unsaturated alkyl and the B ring is saturated, Y is methyl.

2. A compound of claim 1 wherein $R_1$ is methyl.

3. A compound of claim 1 wherein the A ring has a double bond in the 1(2)-position.

4. A compound of claim 1 having a double bond in the 6(7)-position of the B ring.

5. A compound of claim 3 having a double bond in the 6(7)-position of the B ring.

6. A compound of the claim 1 wherein Y is hydrogen.

7. A compound of claim 1 wherein Y is methyl.

8. A compound of claim 1 which is 21-methyl-$\Delta^{1,4,6}$-pregnatriene-20-yne-11$\beta$,17$\beta$-diol-3-one.

9. A process for the preparation of a compound of claim 1 comprising reacting in the presence of alkali metal tertiary tert.-amylate or tert-butylate a compound of the formula

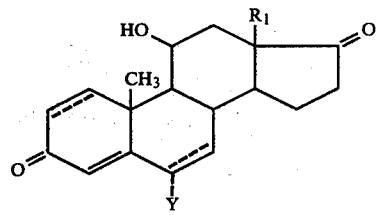

wherein $R_1$, Y and the dotted lines have the above definitions with a compound of the formula HC≡$CR_2$ to obtain the corresponding compounds of claim 1.

10. The process of claim 9 wherein the starting compound has the formula

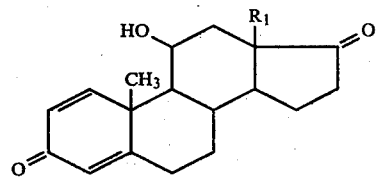

and $R_1$ is alkyl of 1 to 3 carbon atoms.

11. A process for the preparation of a compound of claim 1 comprising reacting a compound of the formula

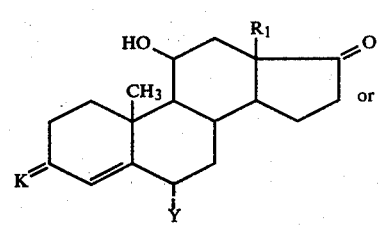

wherein $R_1$ and Y have the above definitions, K is a blocked ketone in the form of a ketal or oxime and L is alkyl of 1 to 12 carbon atoms with a compound of the formula

T—≡$CR_2$ wherein T is selected from the group consisting of lithium, potassium and HalMg— to form a compound of the formula VI or a compound of the formula

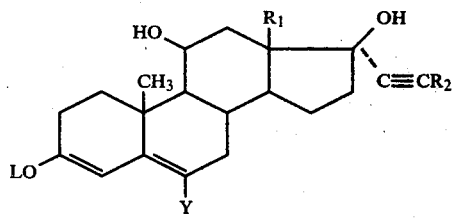

and reacting either the compound of formula VI or VII with an acid hydrolysis agent to obtain a compound of the formula

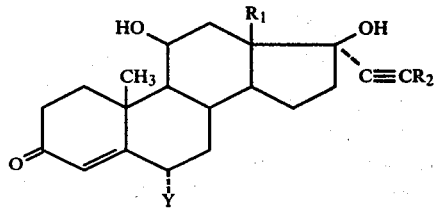

or with p-benzoquinone agent able to free the ketone group and create a $\Delta^{4,6}$-double bond system in aqueous acetone to obtain a compound of the formula

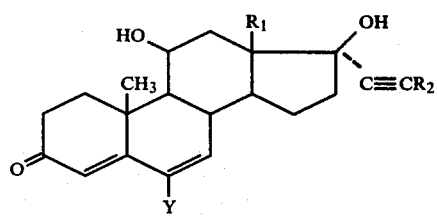

or with p-benzoquinone agent able to free the ketone group and create a $\Delta^{1,4,6}$-double bond system in benzene to obtain a compound of the formula

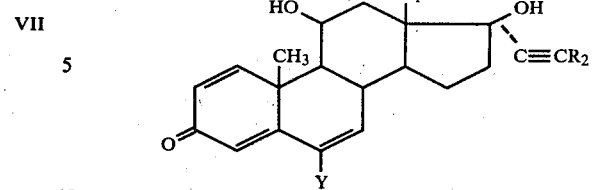

12. 3-ethoxy-6-methyl-$\Delta^{3,5}$-androstadiene-11$\beta$-ol-17-one.

13. An anti-inflammatory composition comprising an anti-inflammatorily effective amount of at least one compound of claim 1 and an inert pharmaceutical carrier.

14. A composition of claim 13 wherein $R_1$ is methyl.

15. A composition of claim 13 wherein the A ring has a double bond in the 1(2)-position.

16. A composition of claim 13 having a double bond in the 6(7)-position of the B ring.

17. A composition of claim 15 having a double bond in the 6(7)-position of the B ring.

18. A composition of claim 13 wherein Y is hydrogen.

19. A composition of claim 13 wherein Y is methyl.

20. A composition of claim 13 which is 21-methyl-$\Delta^{1,4,6}$-pregnatriene-20-yne-11$\beta$,17$\beta$-diol-3-one.

21. A composition of claim 13 wherein the carrier is adapted for topical application to the skin.

22. A method of treating inflammation in warm-blooded animals comprising administering to warm-blooded animals an anti-inflammatorily effective amount of at least one compound of claim 1.

23. The method of claim 22 wherein the compound is applied topically to the skin and/or mucous.

24. A method of claim 22 wherein $R_1$ is methyl.

25. A method of claim 22 wherein the A ring has a double bond in the 1(2)-position.

26. A method of claim 22 having a double bond in the 6(7)-position of the B ring.

27. A method of claim 25 having a double bond in the 6(7)-position of the B ring.

28. A method of claim 22 wherein Y is hydrogen.

29. A method of claim 22 wherein Y is methyl.

30. The method of claim 22 wherein the compound is 21-methyl-$\Delta^{1,4,6}$-pregnatriene-20-yne-11$\beta$,17$\beta$-diol-3-one.

* * * * *

UNITED STATES PATENT AND TRADEMARK OFFICE
CERTIFICATE OF CORRECTION

PATENT NO. : 4,233,297
DATED : November 11, 1980
INVENTOR(S) : JEAN G. TEUTSCH ET AL.

It is certified that error appears in the above—identified patent and that said Letters Patent is hereby corrected as shown below:

Column 2: Between structural formulas (III) and (IV) insert -- or --.

Column 6, line 30: "254°-225°" should read -- 254°-255° --.

Column 10, line 53: "T-$\equiv CR_2$" should read -- T-C$\equiv CR_2$ --.

Signed and Sealed this

Fifth Day of May 1981

[SEAL]

Attest:

RENE D. TEGTMEYER

*Attesting Officer*   *Acting Commissioner of Patents and Trademarks*